United States Patent [19]

Meals

[11] 4,375,809
[45] Mar. 8, 1983

[54] INFLATABLE HAND PILLOW

[76] Inventor: Roy A. Meals, 10376 Keswick Ave., Los Angeles, Calif. 90064

[21] Appl. No.: 210,905

[22] Filed: Nov. 28, 1980

[51] Int. Cl.³ .......................... A61F 5/04; A61F 13/00
[52] U.S. Cl. .................................. 128/90; 128/89 R; 128/133
[58] Field of Search .............. 128/DIG. 20, 89 R, 90, 128/132–134

[56] References Cited

U.S. PATENT DOCUMENTS

| | | | |
|---|---|---|---|
| 2,834,340 | 5/1958 | Walter | 128/DIG. 20 |
| 3,755,820 | 9/1973 | Petrusak | 128/DIG. 30 |
| 3,824,992 | 7/1974 | Nicholson et al. | 128/DIG. 20 |
| 4,266,298 | 5/1981 | Graziano | 128/89 R |

FOREIGN PATENT DOCUMENTS 1171361  11/1969  United Kingdom ....... 128/DIG. 20

*Primary Examiner*—Kyle L. Howell
*Assistant Examiner*—C. W. Shedd
*Attorney, Agent, or Firm*—Nilsson, Robbins, Dalgarn, Berliner, Carson & Wurst

[57] ABSTRACT

An inflatable pillow is disclosed, as for elevating the hand during a period of healing. A pair of inflatable base chamber sections define an L-shape to engage the human upper limb with elbow flexed at an angle of some 90°. A pair of inflatable lateral chamber sections somewhat triangular in profile are affixed at the sides of the L-shaped member for retaining the configuration and providing dimensional cushioning. The interior chambers of the inflatable sections are interconnected, and a flex valve is provided for inflating and deflating the pillow. A pair of strap members bridge the lateral sections to close the pillow about the upper limb. As disclosed, the structure comprises transparent sheet, vinyl-like material.

3 Claims, 4 Drawing Figures

INFLATABLE HAND PILLOW

BACKGROUND AND SUMMARY OF THE INVENTION

During a recovery period for an injured hand, it is usually desirable to raise the hand so that it is in an elevated position with respect to the rest of the patient's body. That is, there is widespread agreement among medical people that elevation of an injured hand (following an accident or operation) is beneficial for: wound healing, recovery of function and patient comfort. With elevation of the hand while the patient is either sitting or recumbent there is provided a nearly continuous balance against hematoma and edema fluid formation.

Traditionally, supporting a patient's hand in an elevated position has involved the use of either slings and overhead hooks or bed pillows. Frequently, both techniques have been used; however, each involves several distinct problems and disadvantages.

The use of a hook and sling is normally suitable only for hospital patients as the safe use of such arrangements requires specialized apparatus and frequent observation. In that regard, hooks and sling supports may have a tendency to pull surgical dressings distally with undesired displacement. Also, the use of such structures involve risks attendant pressure areas and traction blisters. Furthermore, the use of overhead suspension apparatus is normally very confining to the patient and may produce substantial discomfort after a relatively short period of confinement.

Maintaining the hand elevated by the traditional use of stacked bed pillows is also fraught with problems. Stacks of pillows are bulky and difficult to place and maintain in comfortable supporting positions.

Recognizing the problems attendant the use of traditional means for elevating the hand after an accident or injury has resulted in some prior specialized devices for that purpose. Specifically, rigid supports have been proposed as disclosed in U.S. Pat. Nos. 1,643,850; 2,119,325; and 3,528,413. Although useful in certain instances, such supports generally lack the flexibility and comfort which might otherwise be possible for a patient recovering from a hand injury.

Supports have also been proposed in the form of various structures of foam material as disclosed, for example, in U.S. Pat. No. DE. 247,311. Although such supports are useful in certain situations, again attendant disadvantages have existed. Specifically, such structures in various forms have been rather bulky resulting in difficulty both for manipulation and storage. Some such devices have accommodated only limited positions for the patient and have not only concealed the hand from inspection but have also blocked a substantial portion of the patient's visual view. Accordingly, a need has continued to exist for an improved hand-elevating support apparatus.

In general, the present invention is directed to an inflatable support pillow. Of course, various forms of inflatable pillows have been previously proposed to accommodate specific body members. For example, one such pillow structure is disclosed in U.S. Pat. No. 3,584,914. Such apparatus have not accommodated the principal objective of the present invention which resides in elevating an injured hand with relative convenience by affording cushioning and a wide variety of possible positions. Additionally, the apparatus of the present invention is convenient to use, store, and clean, and exposes the hand for inspection and access to most wounds.

In general, the pillow of the present invention is formed of transparent inflatable sections to define a width of space of somewhat triangular shape for receiving a patient's upper limb when flexed at the elbow to approximately 90°. The hypotenuse side of the triangular space is open to be bridged by straps which affix the pillow to the patient's upper limb. The posterior surface of the arm rests on a rectangular cushion section coinciding to a short leg of the triangular configuration while the ulnar border of the patient's forearm rests against a longer perpendicular cushion section. Inflatable lateral chamber sections are integrally formed with the angled cushion sections to complete the pillow structure defining the triangular space.

BRIEF DESCRIPTION OF THE DRAWINGS

In the drawings, which constitute a part of this specification, an exemplary embodiment demonstrating various objectives and features hereof is set forth as follows.

DESCRIPTION OF THE ILLUSTRATIVE EMBODIMENT

As indicated above, a detailed illustrative embodiment of the invention is disclosed herein. However, embodiments may be constructed in accordance with various forms, some of which may be rather different from the disclosed illustrative embodiment. Consequently, the specific structural and functional details disclosed herein are merely representative, yet in that regard they are deemed to provide the best embodiment for purposes of disclosure and to provide a basis for the claims herein which define the scope of the present invention.

Figure 1:
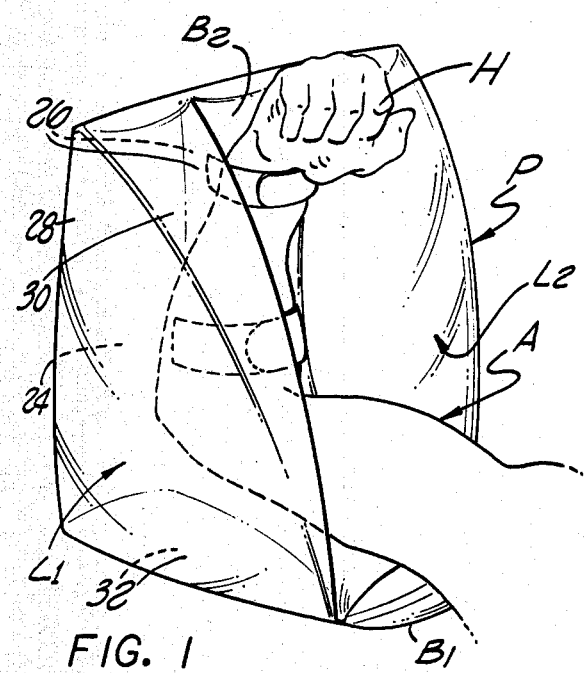
FIG. 1 is a perspective view of an inflatable support pillow constructed in accordance with the present invention.

Referring initially to FIG. 1, a pillow P is illustrated affixed on the upper limb A of a human patient. Generally, the pillow affords support for the upper limb (specifically with the hand H elevated) in a wide variety of different positions. Cushioned support is afforded by a pair of base chamber sections B1 and B2 (see FIG. 3) which define an L-shaped cushion configuration.

A pair of similar lateral chamber sections L1 and L2 (FIG. 4) are integral with the base chamber sections B1 and B2 to close the sides of the L-shaped configuration completing the pillow P.

While the upper limb A is illustrated in FIG. 1 with the forearm substantially vertical, it can be seen that a wide variety of positions are accommodated. Specifically, the forearm may be horizontally positioned to rest on the cushion afforded by each of the other chamber sections.

Considering the pillow P in greater detail, the different chamber sections may be variously formed in accordance with a wide variety of plastic fabrication techniques. In that regard, while the individual chamber sections have been identified above for purposes of explanation, and will be referred to below, it is to be understood that such sections are not necessarily related to any particular configuration of sheets or panels of sheet material in a specific embodiment of the pillow.

The pillow P may be formed to incorporate panels of transparent vinyl-like material in a wide variety of different patterns and scenes. The important consideration resides in the integral pillow defining the component sections as indicated above. In that regard, specific sheets of material may or may not coincide with individual panels as discussed in detail below.

Figure 4:
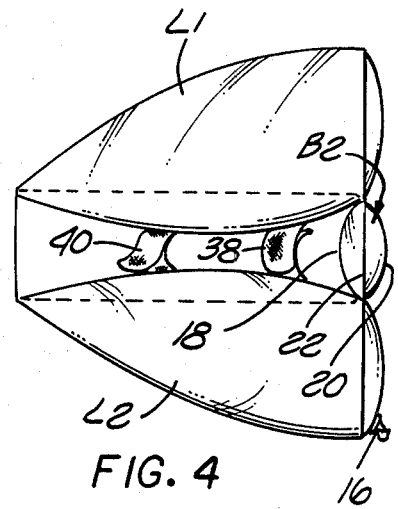
FIG. 4 is a top plan view of the pillow of FIG. 1.
Figure 2:
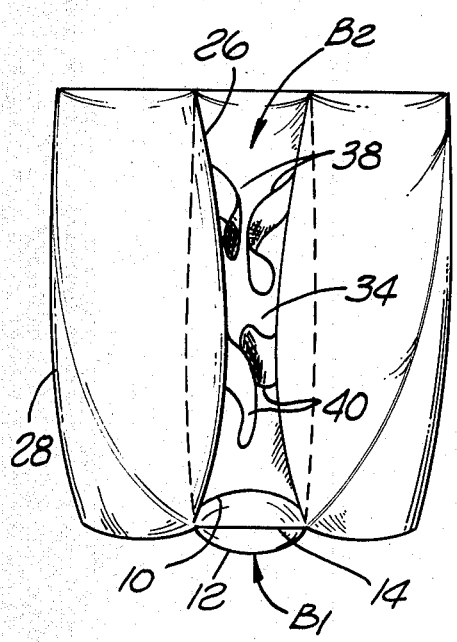
FIG. 2 is a front elevation of the pillow of FIG. 1.
Figure 3:
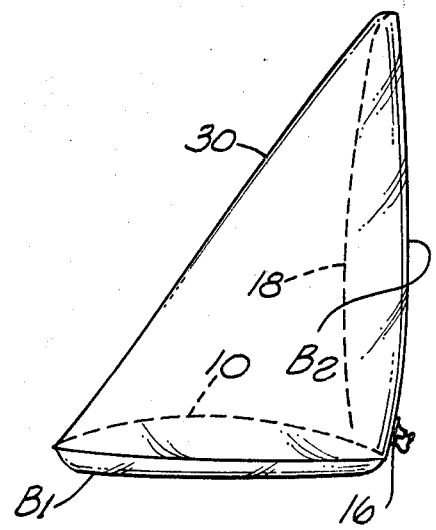
FIG. 3 is a side elevation of the pillow of FIG. 1.

The base chamber sections B1 and B2 each comprise a pair of mated panels of thin, transparent, inflatable sheet material, e.g. vinyl. Although depicted in an inflated configuration for clearer presentation, the panels are actually formed as flat sheets. Specifically, the base chamber section B1 comprises a pair of mating rectangular sheet panels 10 and 12 (FIG. 2, bottom). These panels are edge joined as indicated by a seam 14 to define the inflatable chamber. Note that the seams in the pillow P, as described below are partly open to interconnect all of the chambers for inflation through a single plastic flex valve 16 (FIGS. 3 and 4).

At the rear end of the base chamber section B1 (FIG. 2), that member joins with the base chamber section B2 at an apex 17 (FIG. 3) to define an L-shaped support for engaging the flexed upper limb A as illustrated in FIG. 1. The base chamber section B2 (FIG. 4) also comprises a mated pair of flexible, transparent sheet panels, specifically a pair of longer panels 18 and 20 as illustrated in FIG. 4 are peripherally joined by a seam 22.

The L-shaped combination of the base chamber sections B1 and B2 is integrally connected with the lateral chamber sections L1 and L2. Structurally, the lateral chamber sections L1 and L2 each defines a triangular profile, the solid form of which is an irregular pyramid with a trapezoidal base. The lateral sections L1 and L2 are attached along the L-shaped elongate seams of the base chamber sections B1 and B2.

The irregular pyramidal shapes of the lateral chamber sections L1 and L2 may be best appreciated by considering the lateral chamber section L1 as exemplary and as depicted in FIG. 1. Specifically, the irregular pyramidal configuration is defined by a trapezoidal base panel 24, a pair of relatively large opposed triangular panels 26 and 28, and the dissimilar narrow triangular panels 30 and 32. The lateral chamber section L2 is a mirror image of the lateral chamber section L1 and accordingly is formed with the individual panels as described above with regard to the lateral chamber section L1.

In the composite pillow, the lateral chamber sections L1 and L2 close the angle (substantially 90°) defined by the L-shaped combination of the base chamber sections B1 and B2. Consequently, the composite pillow defines a somewhat triangular space 34 (FIG. 2) of varying thickness. Specifically, adjacent to the base chamber sections B1 and B2, the space 34 is sufficiently wide to accommodate the upper limb A. However, moving outward from the closed apex of the triangular space 34, the thickness of the space is diminished by the ovoid curvature of the internal panels, e.g. panel 26. Consequently, an L-shaped channel is defined adjacent to the base chamber sections B1 and B2 for receiving the upper limb A.

To retain the upper limb A (FIG. 1) in the space 34, two pairs of mating straps are affixed to the interior sides of the lateral chamber sections L1 and L2. The mating or lapping surfaces 42 of the straps 38 and 40 carry Velcro, for mutual attachment.

As indicated above, in the manufacture of the composite inflatable support pillow, a variety of production techniques as well known in the sheet-fabricating arts may be employed. Normally, the composite pillow will be reduced to a pattern of plain surfaces which can be employed to produce sheets definitive of the panels as described above and in turn for forming the composite pillow. In an existing embodiment of the invention, as well as the illustrative embodiment, the panels of the pillow are formed entirely of thin, impermeable transparent vinyl sheeting. Various joining techniques may be employed to accomplish the desired seams for developing the composite pillow as explained above. Of course, similar joining techniques may be employed to affix the straps 38 and 40 to the sheet material.

With the completion of the composite pillow, in a deflated state, the unit occupies relatively little space and may be very conveniently packaged, shipped, and stored. When ready for use, inflation is by the flex valve 16 which may be of the type commonly employed in plastic sheet toys and when closed may be forced into the inflated space. Of course, when inflated, the chambers all assume somewhat circular configurations in cross section as a result of the balloon effect. Such shaping tends to define the space 34 for the upper limb A and to accomplish the desired cushioning.

Of course, varying dimensions may accommodate different pillows for specific applications. However, it has generally been determined that the lateral chamber sections L1 and L2 should develop a cushion thickness in excess of two inches while the base chamber sections B1 and B2 should develop a cushion thickness in excess of one inch. In the existing embodiment, the cushion thickness of the base chambers approaches two inches while the thickness of the lateral chamber sections approaches three inches. These thicknesses are also significant in maintaining the desired elevation when the upper limb A is placed in certain positions.

After inflating the pillow P, it is placed on the upper limb A (flexed at the elbow to approximately 90°) as illustrated. Thus, the upper limb A is fitted into the space 34 (FIG. 2) adjacent to the base chamber sections B1 and B2. The posterior surface of the upper limb A rests on the shorter base chamber section B1 and the ulnar border of the forearm dwells against the longer base chamber section B2. The end surfaces 42 of the straps 38 and 40 are then mated securing the pillow P to the upper limb A in the antecubital and wrist areas.

The dimensions of the pillow P along with its flexibility comfortably accommodate the limb even when a bulky dressing is carried. Note also that the convexity of the internal panels in the lateral chamber sections L1 and L2 gently wedge the limb into the depths of the space 34. Perhaps more importantly, the shapes of the lateral chamber sections L1 and L2 maintain the hand in an elevated position accommodating the patient in a variety of sitting and lying positions. For example, the hand H is well elevated above the level of the heart when the patient is supine with the shoulder in neutral rotation and any degree of abduction.

The pillow also maintains good elevation of the hand with any degree of shoulder rotation and even when the patient lies on either side. In the fully prone position, the hand is still elevated, but the forced internal or external rotation of the shoulder which is required makes this position uncomfortable for long periods of time.

When seated, a patient can comfortably rest the panel B1 (FIG. 1) on a table or other support surface maintaining the hand H well elevated. Thus, in addition to providing elevated support for the hand H in a wide variety of different body and shoulder positions, the pillow P has other distinct advantages. Obviously, the pillow does not require any form of overhead hook or sling arrangement. Furthermore, the pillow is well suited for home use, and is easily stored, cleaned, placed on the patient and removed. The pillow involves negligible risk of pressure areas or traction blisters and offers almost no interference to surgical dressings. Still further, the pillow is exceedingly light in weight and in a transparent form the patient's view is unobstructed so that he can easily move about without disturbing nearby objects or impacting his wound. The transparent pillow also allows for inspection of the entire surgical dressing and any uncovered areas of skin without removing the limb from the pillow.

It may therefore be seen that the support pillow of the present invention affords a very useful, economical, convenient, safe, and comfortable structure for supporting the human hand in an elevated position. Of course, the apparatus can be implemented using a wide variety of different techniques and materials, and in that regard it is to be appreciated that the pillow as presented herein is merely an illustrative embodiment deemed best for present purposes, however, recognizing that the scope hereof shall be in accordance with the claims and equivalents as set forth below.

What is claimed is:

1. An air pillow for the human upper limb, comprising:
    inflatable base chamber sections extending in an angular relationship to provide cushion surfaces for the arm and forearm when flexed;
    a pair of inflatable lateral chamber sections formed of transparent, flexible sheet material and affixed at the sides of said base chamber sections bridging the angle therebetween and defining therewith an angular space to receive said upper limb and positioned to support the distal portion of said upper limb therebetween and in an upright position;
    means for inflating and deflating said chamber sections; and
    closure means including at least one strap closure affixed between said pair of lateral chamber sections.

2. A pillow according to claim 1 wherein said chamber sections are internally interconnected and wherein said means for inflating and deflating comprises a flex valve mounted in one of said chamber sections.

3. A pillow according to claim 1 wherein said base chamber sections comprise opposed, edge-sealed sheets of flexible material substantially rectangular in configuration and said lateral chamber sections comprise spaced-apart opposed sheets of flexible material of substantially triangular configuration.

* * * * *